US009451928B2

(12) United States Patent
Falco et al.

(10) Patent No.: US 9,451,928 B2
(45) Date of Patent: Sep. 27, 2016

(54) INCORPORATING INTERNAL ANATOMY IN CLINICAL RADIOTHERAPY SETUPS

(75) Inventors: Tony Falco, La Prairie (CA); Martin Lachaine, Montreal (CA); Jason Gorman, Tucson, AZ (US)

(73) Assignee: Elekta LTD., Montreal, Quebec (CA)

( * ) Notice: Subject to any disclaimer, the term of this patent is extended or adjusted under 35 U.S.C. 154(b) by 702 days.

(21) Appl. No.: 11/852,492

(22) Filed: Sep. 10, 2007

(65) Prior Publication Data

US 2008/0064953 A1 Mar. 13, 2008

Related U.S. Application Data

(60) Provisional application No. 60/844,163, filed on Sep. 13, 2006.

(51) Int. Cl.
| | |
|---|---|
| *G01N 23/04* | (2006.01) |
| *A61B 8/08* | (2006.01) |
| *A61N 5/10* | (2006.01) |
| *A61B 5/055* | (2006.01) |
| *A61B 6/03* | (2006.01) |

(52) U.S. Cl.
CPC .............. *A61B 8/08* (2013.01); *A61B 8/483* (2013.01); *A61N 5/1049* (2013.01); *A61B 5/055* (2013.01); *A61B 6/03* (2013.01); *A61N 2005/1058* (2013.01)

(58) Field of Classification Search
USPC ....... 600/407, 425, 426, 427, 436, 437, 439, 600/440, 443, 1, 2, 411; 378/65
See application file for complete search history.

(56) References Cited

U.S. PATENT DOCUMENTS

| | | | |
|---|---|---|---|
| 3,082,322 A | 3/1963 | Koerner et al. |
| 3,777,124 A | 12/1973 | Pavkovich |
| 3,987,281 A | 10/1976 | Hodes |
| 3,991,310 A | 11/1976 | Morrison |
| 4,118,631 A | 10/1978 | Froggatt |
| 4,618,978 A | 10/1986 | Cosman |
| 4,882,741 A | 11/1989 | Brown |
| 4,923,459 A | 5/1990 | Nambu |
| 4,943,990 A | 7/1990 | Schar |
| 5,039,867 A | 8/1991 | Nishihara et al. |

(Continued)

FOREIGN PATENT DOCUMENTS

| | | |
|---|---|---|
| CA | 2416887 A1 | 2/2002 |
| CA | 2621741 A1 | 3/2007 |

(Continued)

OTHER PUBLICATIONS

International Search Report for International application No. PCT/CA2007/001626 dated Jan. 3, 2008 (4 pages).

(Continued)

*Primary Examiner* — Tse Chen
*Assistant Examiner* — Jason Ip
(74) *Attorney, Agent, or Firm* — Finnegan, Henderson, Farabow, Garrett & Dunner, LLP (57) ABSTRACT

A diagnostic image of internal anatomical features of a patient is annotated with representations of external features, such that both can be viewed together on a visual display. Adjustments to various treatment parameters relating to the administration of radiation therapy are provided, and the displayed image is automatically updated based on the adjustments.

21 Claims, 4 Drawing Sheets

(56) References Cited

U.S. PATENT DOCUMENTS

| | | |
|---|---|---|
| 5,080,100 A | 1/1992 | Trotel |
| 5,086,401 A | 2/1992 | Glassman et al. |
| 5,099,846 A | 3/1992 | Hardy |
| 5,107,839 A | 4/1992 | Houdek et al. |
| 5,117,829 A | 6/1992 | Miller et al. |
| 5,138,647 A | 8/1992 | Nguyen et al. |
| 5,207,223 A | 5/1993 | Adler |
| 5,222,499 A | 6/1993 | Allen et al. |
| 5,233,990 A | 8/1993 | Barnea |
| 5,291,889 A | 3/1994 | Kenet et al. |
| 5,295,483 A | 3/1994 | Nowacki et al. |
| 5,299,288 A | 3/1994 | Glassman et al. |
| 5,301,674 A | 4/1994 | Erikson et al. |
| 5,379,642 A | 1/1995 | Reckwerdt et al. |
| 5,389,101 A | 2/1995 | Heilbrun et al. |
| 5,391,139 A | 2/1995 | Edmundson |
| 5,397,329 A | 3/1995 | Allen |
| 5,408,101 A | 4/1995 | Wong |
| 5,411,026 A | 5/1995 | Carol |
| 5,438,991 A * | 8/1995 | Yu et al. ............... 600/426 |
| 5,442,675 A | 8/1995 | Swerdloff et al. |
| 5,446,548 A | 8/1995 | Gerig et al. |
| 5,447,154 A | 9/1995 | Cinquin et al. |
| 5,483,961 A | 1/1996 | Kelly et al. |
| 5,511,549 A | 4/1996 | Legg et al. |
| 5,524,627 A | 6/1996 | Passi |
| 5,528,650 A * | 6/1996 | Swerdloff et al. ......... 378/65 |
| 5,531,227 A | 7/1996 | Schneider |
| 5,531,520 A | 7/1996 | Grimson et al. |
| 5,553,618 A | 9/1996 | Suzuki et al. |
| 5,591,983 A | 1/1997 | Yao |
| 5,603,318 A | 2/1997 | Heilbrun et al. |
| 5,609,485 A | 3/1997 | Bergman et al. |
| 5,645,066 A | 7/1997 | Gandini et al. |
| 5,673,300 A | 9/1997 | Reckwerdt et al. |
| 5,690,108 A | 11/1997 | Chakeres |
| 5,692,507 A * | 12/1997 | Seppi et al. ............ 128/653.1 |
| 5,715,166 A | 2/1998 | Besl et al. |
| 5,734,384 A | 3/1998 | Yanof et al. |
| 5,740,225 A * | 4/1998 | Nabatame ............... 378/65 |
| 5,754,623 A | 5/1998 | Seki |
| 5,757,881 A | 5/1998 | Hughes |
| 5,778,043 A | 7/1998 | Cosman |
| 5,810,007 A | 9/1998 | Holupka et al. |
| 5,836,954 A | 11/1998 | Heilbrun et al. |
| 5,851,183 A | 12/1998 | Bucholz |
| 5,859,891 A | 1/1999 | Hibbard |
| 5,871,445 A | 2/1999 | Bucholz |
| 5,952,577 A | 9/1999 | Passi |
| 5,991,703 A | 11/1999 | Kase |
| 6,019,724 A | 2/2000 | Gronningsaeter et al. |
| 6,038,283 A | 3/2000 | Carol et al. |
| 6,094,508 A | 7/2000 | Acharya et al. |
| 6,106,470 A | 8/2000 | Geiser et al. |
| 6,112,341 A | 9/2000 | Moreland |
| 6,117,081 A | 9/2000 | Jago et al. |
| 6,118,848 A | 9/2000 | Reiffel |
| 6,119,033 A | 9/2000 | Spigelman et al. |
| 6,122,341 A | 9/2000 | Butler et al. |
| 6,129,670 A | 10/2000 | Burdette et al. |
| 6,138,495 A | 10/2000 | Paltieli et al. |
| 6,144,875 A | 11/2000 | Schweikard et al. |
| 6,146,390 A | 11/2000 | Heilbrun et al. |
| 6,198,957 B1 | 3/2001 | Green |
| 6,208,883 B1 | 3/2001 | Holupka et al. |
| 6,259,943 B1 | 7/2001 | Cosman et al. |
| 6,269,143 B1 | 7/2001 | Tachibana |
| 6,285,805 B1 | 9/2001 | Gueziec |
| 6,292,578 B1 | 9/2001 | Kalvin |
| 6,307,914 B1 | 10/2001 | Kunieda et al. |
| 6,314,310 B1 | 11/2001 | Ben-Haim et al. |
| 6,325,758 B1 | 12/2001 | Carol et al. |
| 6,345,114 B1 | 2/2002 | Mackie et al. |
| 6,359,959 B1 | 3/2002 | Butler et al. |
| 6,366,798 B2 | 4/2002 | Green |
| 6,385,286 B1 | 5/2002 | Fitchard et al. |
| 6,385,288 B1 | 5/2002 | Kanematsu |
| 6,390,982 B1 | 5/2002 | Bova et al. |
| 6,405,072 B1 | 6/2002 | Cosman |
| 6,423,009 B1 | 7/2002 | Downey et al. |
| 6,438,202 B1 | 8/2002 | Olivera et al. |
| 6,459,769 B1 | 10/2002 | Cosman |
| 6,491,702 B2 | 12/2002 | Heilbrun et al. |
| 6,511,430 B1 | 1/2003 | Sherar et al. |
| 6,516,046 B1 | 2/2003 | Frohlich et al. |
| 6,535,574 B1 | 3/2003 | Collins et al. |
| 6,546,073 B1 | 4/2003 | Lee |
| 6,553,152 B1 | 4/2003 | Miller et al. |
| 6,560,311 B1 | 5/2003 | Shepard et al. |
| 6,567,684 B1 | 5/2003 | Chenevert et al. |
| 6,585,651 B2 | 7/2003 | Nolte et al. |
| 6,591,127 B1 | 7/2003 | McKinnon |
| 6,600,810 B1 | 7/2003 | Hughes |
| 6,621,889 B1 | 9/2003 | Mostafavi |
| 6,628,983 B1 | 9/2003 | Gagnon |
| 6,631,284 B2 | 10/2003 | Nutt et al. |
| 6,636,622 B2 | 10/2003 | Mackie et al. |
| 6,641,539 B2 | 11/2003 | Hirooka et al. |
| 6,661,870 B2 | 12/2003 | Kapatoes et al. |
| 6,662,036 B2 | 12/2003 | Cosman |
| 6,669,635 B2 | 12/2003 | Kessman et al. |
| 6,683,985 B1 | 1/2004 | Kase et al. |
| 6,690,965 B1 | 2/2004 | Riaziat et al. |
| 6,714,627 B1 | 3/2004 | Brown et al. |
| 6,725,079 B2 | 4/2004 | Zuk et al. |
| 6,728,424 B1 | 4/2004 | Zhu et al. |
| 6,731,970 B2 | 5/2004 | Schlossbauer et al. |
| 6,750,873 B1 | 6/2004 | Bernardini et al. |
| 6,754,374 B1 | 6/2004 | Miller et al. |
| 6,785,409 B1 | 8/2004 | Suri |
| 6,804,548 B2 | 10/2004 | Takahashi et al. |
| 6,914,959 B2 | 7/2005 | Bailey et al. |
| 6,915,008 B2 | 7/2005 | Barman et al. |
| 6,968,224 B2 | 11/2005 | Kessman et al. |
| 6,980,679 B2 | 12/2005 | Jeung et al. |
| 7,092,109 B2 | 8/2006 | Satoh et al. |
| 7,095,823 B2 | 8/2006 | Topolnjak et al. |
| 7,260,426 B2 | 8/2007 | Schweikard et al. |
| 7,333,644 B2 | 2/2008 | Jerebko et al. |
| 7,343,030 B2 | 3/2008 | Sawyer |
| 7,430,321 B2 | 9/2008 | Okada et al. |
| 7,438,685 B2 | 10/2008 | Burdette et al. |
| 7,535,411 B2 | 5/2009 | Falco |
| 7,613,501 B2 | 11/2009 | Scherch |
| 7,634,304 B2 | 12/2009 | Falco et al. |
| 7,662,097 B2 | 2/2010 | Falco et al. |
| 7,672,705 B2 | 3/2010 | Lachaine et al. |
| 7,729,744 B2 | 6/2010 | Falco et al. |
| 7,801,349 B2 | 9/2010 | Wang et al. |
| 2001/0035871 A1 | 11/2001 | Bieger et al. |
| 2001/0049475 A1 | 12/2001 | Bucholz et al. |
| 2002/0018588 A1 | 2/2002 | Kusch |
| 2002/0065461 A1 | 5/2002 | Cosman |
| 2002/0082494 A1 | 6/2002 | Balloni et al. |
| 2002/0087101 A1* | 7/2002 | Barrick et al. ............ 600/587 |
| 2002/0122530 A1 | 9/2002 | Erbel et al. |
| 2002/0156375 A1 | 10/2002 | Kessman et al. |
| 2002/0176541 A1 | 11/2002 | Schubert et al. |
| 2002/0183610 A1 | 12/2002 | Foley et al. |
| 2002/0188194 A1 | 12/2002 | Cosman |
| 2003/0018232 A1 | 1/2003 | Elliott et al. |
| 2003/0028401 A1 | 2/2003 | Kaufman et al. |
| 2003/0112922 A1 | 6/2003 | Burdette et al. |
| 2003/0144813 A1 | 7/2003 | Takemoto et al. |
| 2003/0153825 A1 | 8/2003 | Mooradian et al. |
| 2003/0182072 A1 | 9/2003 | Satoh et al. |
| 2003/0231790 A1 | 12/2003 | Bottema |
| 2004/0015075 A1 | 1/2004 | Kimchy et al. |
| 2004/0015176 A1 | 1/2004 | Cosman |
| 2004/0034301 A1 | 2/2004 | Falco |
| 2004/0092815 A1 | 5/2004 | Schweikard et al. |
| 2004/0146137 A1 | 7/2004 | Bruder et al. |
| 2004/0152975 A1* | 8/2004 | Blevis ............... 600/427 |
| 2004/0176925 A1 | 9/2004 | Satoh et al. |

(56) References Cited

U.S. PATENT DOCUMENTS

| | | |
|---|---|---|
| 2004/0184646 A1 | 9/2004 | Oosawa |
| 2004/0252870 A1 | 12/2004 | Reeves et al. |
| 2004/0260142 A1 | 12/2004 | Lovoi |
| 2005/0020917 A1 | 1/2005 | Scherch |
| 2005/0096535 A1* | 5/2005 | de la Barrera ............... 600/424 |
| 2005/0180544 A1 | 8/2005 | Sauer et al. |
| 2005/0251029 A1 | 11/2005 | Khamene et al. |
| 2006/0020195 A1 | 1/2006 | Falco et al. |
| 2006/0074292 A1 | 4/2006 | Thomson et al. |
| 2006/0093205 A1 | 5/2006 | Bryll et al. |
| 2006/0120608 A1 | 6/2006 | Luo et al. |
| 2006/0241443 A1 | 10/2006 | Whitmore et al. |
| 2006/0270934 A1* | 11/2006 | Savord et al. ............... 600/437 |
| 2006/0285641 A1 | 12/2006 | Scherch |
| 2006/0293583 A1 | 12/2006 | Saracen et al. |
| 2007/0015991 A1 | 1/2007 | Fu et al. |
| 2007/0038058 A1 | 2/2007 | West et al. |
| 2007/0055090 A1 | 3/2007 | Neustadter et al. |
| 2008/0039713 A1 | 2/2008 | Thomson et al. |
| 2008/0064953 A1 | 3/2008 | Falco et al. |
| 2008/0098322 A1* | 4/2008 | Champion et al. ........... 715/771 |
| 2008/0219405 A1 | 9/2008 | Falco et al. |
| 2008/0292194 A1 | 11/2008 | Schmidt et al. |
| 2009/0003523 A1 | 1/2009 | Raanes et al. |
| 2009/0093716 A1 | 4/2009 | Deischinger et al. |
| 2009/0110145 A1 | 4/2009 | Lu et al. |
| 2011/0069815 A1 | 3/2011 | Nord et al. |

FOREIGN PATENT DOCUMENTS

| | | |
|---|---|---|
| EP | 0647457 A1 | 4/1995 |
| EP | 951697 A1 | 10/1999 |
| EP | 1304960 A1 | 5/2003 |
| EP | 1426806 A2 | 6/2004 |
| EP | 1757228 A1 | 2/2007 |
| FR | 2778574 | 11/1999 |
| JP | 2006000220 A | 1/2006 |
| WO | WO-992074 A1 | 1/1999 |
| WO | WO-9906644 A1 | 2/1999 |
| WO | WO-9926534 A1 | 6/1999 |
| WO | WO-9927839 A2 | 6/1999 |
| WO | WO-0105316 A1 | 1/2001 |
| WO | WO-0209588 A1 | 2/2002 |
| WO | WO-03/039370 A1 | 5/2003 |
| WO | WO-03076003 A2 | 9/2003 |
| WO | WO-2006051523 A2 | 5/2006 |

OTHER PUBLICATIONS

Written Opinion of the International Searching Authority for International application No. PCT/CA2007/001626 dated Dec. 21, 2007 (7 pages).
Besl et al., A Method for Registration of 3d Shapes, IEEE Transactions on Pattern Analysis and Machine Intelligence 14(2):239-256 (1992).
Booth, Modelling, the impact of treatment uncertainties in radiotherapy, University of Adelaide, Mar. 2002), Section 2.4 (http://thesis.library.adelaide.edu.au/uploads/approved/adt-SUA20020816.175301/public/03_chapter2.pdf.
Brujic et al., Analysis of Free-Form Surface Registration, International Conference on Image Processing, pp. 393-396 (1996).
Cuisenaire, O., http)/www.tele.ucl.ac.be/PEOPLE/OC/these/node74.html, <http://www.tele.ucl.ac.be/PEOPLE/OC/these/node74.html,> Posted Oct. 5, 1999, Downloaded from the Internet on Aug. 10, 2004.
Cuisenaire, O., <http://www.tele.ucl.ac.be/PEOPLE/OC/these/node75.html,> Posted Oct. 5, 1999, Downloaded from the Internet on Aug. 10, 2004.
Cuisenaire, O., <http://www.tele.ucl.ac.be/PEOPLE/OC/these/node12.html,> Posted Oct. 5, 1999, Downloaded from the Internet on Aug. 10, 2004.
Dubois et al. Intraobserver and Interobserver Variability of MR Imaging- and CT-derived Prostate Volumes after Transperineal Interstitial Permanent Prostate Brachytherapy, Radiology. 207(3):785-9 (1998).
Eggert et al., Simultaneous Registration of Multiple Range Views for Reverse Engineering, International Conference of Pattern Recognition, pp. 243-247 (1996).
Hanks, et al.,Clinical and Biochemical Evidence of Control of Prostate Cancer at 5 Years After External Beam Radiation, The Journal of Urology, vol. 154, 456-459 (1995).
Haralick et al., Pose Estimation From Corresponding Data Point, IEEE Transactions on Systems, Man, and Cybernetics, 19(6):1426-1446 (1989).
Hua et al., Development of a Semi-Automatic Alignment Tool for Accelerated Localization of the Prostate, Int. J. Radiation Oncology Biol. Phys., 55(3):811-823 (2003).
Jiang et al., A New Approach to 3-d Registration of Multimodality Medical Images by Surface Matching, SPIE vol. 1808 Visualization in Biomedical Computing,, pp. 196-213 (1992).
Michalski et al., Three-Dimensional Conformal Radiation Therapy (3DCRT) for Prostate Cancer, Radiation Oncology Center, Mallinckrodt Institute of Radiology, Washington University Medical Center, St. Louis, Missouri (1996) http://www.phoenix5 org/Infolink/Michalski/#3.
Paskalev et al., Daily Target Localization for Prostate Patients based on 3-D Image Correlation, Phys. Med. Biol., vol. 49, pp. 931-939 (2004).
Pennec et al,. A Framework for Uncertainty and Validation of 3-D Registration Methods Based on Points and Frames, International Journal of Computer Vision 25(3), 203-229 (1997).
Aoki, Y. et al. An Integrated Radiotherapy Treatment System and its Clinical Application, Radiation Medicine, vol. 5, No. 4, pp. 131-141, 1987.
Barratt, Dean C., "Accuracy of an Electromagnetic Three-Dimensional Ultrasound System for Carotid Artery Imaging" from Ultrasound in Medicine and Biology, vol. 27, No. 10, 2001, pp. 1421-1425.
Bijhold, J. et al. Fast evaluation of patient set-up during radiotherapy by aligning features in portal and simulator images, Phys. Med. Biol., 1999, vol. 36, No. 12, pp. 1665-1679.
Bijhold, J. Three-dimensional verification of patient placement during radiotherapy using portal images, Med. Phys. 20 (2), Pt. 1, Mar./Apr. 1993. pp. 347-356.
Boctor, et al., A Rapid Calibration Method for Registration and 3D Tracking of Ultrasound Images Using Spatial Localizer, Proceedings of the SPIE (2003).
Boyer, A. A review of electronic portal imaging devices (EPIDs), Med. Phys. 19 (1), Jan./Feb. 1992 pp. 1-16.
Brigger, et al., "B-Spline Snakes: A Flexible Tool for Parametric Contour Detection," IEEE Transactions on Image Processing, vol. 9, No. 9, Sep. 2000, pp. 1484-1496.
Brunie L. et al. Pre-and intra-irradiation multimodal image registration: principles and first experiments, Radiotherapy and Oncology 29 (1993) pp. 244-252.
Christensen G. E., Inverse consistent registration with object boundary constraints, Biomedical Imaging: Macro to Nano, 2004, IEEE International Symposium on Arlington, VA, USA Apr. 15-18, 2004, Piscataway, NJ, USA, IEEE (4 pages).
Claim Chart for Claim 10 of U.S. Pat. No. 5,447,154.
Cuadra, M.B. et al., Atlas-based Segmentation of pathological MR brain images using a model of lesion growth; Medical Imaging IEEE Transactions on, vol. 23, No. 10, pp. 1301-1314, Oct. 2004.
Czarnota G.J. et al. Ultrasound imaging of apoptosis: high-resolution non-invasive monitoring of programmed cell death in vitro, in situ and in vivo, British Journal of Cancer (1999) 81(3), pp. 520-527.
European Search Report for European Patent Application No. 07815820.1 (PCT/CA2007/001626) dated Nov. 5, 2010 (6 pages).
Holupka, et al., (1996), "Ultrasound Image Fusion for External Beam Radiotherapy for Prostate Cancer," J. Radiation Oncology Biol. Phys., vol. 35, No. 5, pp. 975-984.
International Preliminary Report on Patentability for International Application No. PCT/CA2005/001106 dated Jan. 23, 2007.

(56) References Cited

OTHER PUBLICATIONS

International Preliminary Report on Patentability for PCT/CA2005/001428 dated Oct. 3, 2007 (1 page).
International Search Report and Written Opinion for International Application No. PCT/CA2010/002008 dated May 2, 2012, 7 pages.
International Search Report and Written Opinion for PCT/CA2009/000750, mailed Sep. 18, 2009 (8 pages).
International Search Report for PCT/CA10/002008, mailed May 2, 2012, (4 pages).
International Search Report for PCT/CA2005/001106 dated Nov. 15, 2005.
International Search Report for PCT/CA2005/001428 dated Nov. 16, 2005.
International Search Report for PCT/CA2005/01105 dated Oct. 27, 2005.
International Search Report for PCT/CA2006/001289 dated Oct. 30, 2006 (3 pages).
International Search Report for PCT/CA2006/001461 dated Nov. 30, 2006 (5 pages).
International Search Report for PCT/CA2007/000898 dated Jul. 12, 2007 (3 pages).
Leszczynski K W et al., "An Image Registration scheme applied to verification of radiation therapy" British Journal of Radiology British Inst. Radiol UK [Online] vol. 71, No. 844, Apr. 1998, ISSN: 0007-1285, retrieved from the Internet: url:http://bjr.birjournals.org/cgi/reprint/71/844/413.pdf. [retrieved on Nov. 10, 2009].
Lizzi, Frederic, et al., "Ultrasonic Spectrum Analysis of Tissue Assays and Therapy Evaluation," International Journal of Imaging Systems and Technology, Wiley and Sons, New York, vol. 8, No. 1, (Jan. 1, 1997), pp. 3-10.
Maurer C R et al., Registration of 3-D Images Using Weighted Geometrical Features, IEEE Transactions on Medical Imaging, IEEE Service Center, Piscataway, NJ, US vol. 15, No. 6, Dec. 1, 1996 (14 pages).
Meertens, H. et al. A method for the measurement of field placement errors in digital portal images, Phys. Med. Biol., 1990, vol. 35, No. 3, pp. 299-323.
Mencarelli, et al., "A Dosimetric Method to derive optimal couch corrections in the presence of anatomical deformations for H & N cancer," abstract, 2011, 2 pages.
Nagel, et al., "Online dose-guided setup correction protocol for hypo fractionated lung radiotherapy," abstract, 2009, 1 page.
Pito, A Registration Aid, International Conference on Recent Advanced in 3D Digital Imaging and Modelling, pp. 85-92 (1997).
Reinstein, L. et al. Radiotherapy Portal Imaging Quality, Report of AAPM Task Group No. 28, American Association of Physicists in Medicine by the American Institute of Physics, New York, 1988.
Robb, Three-Dimensional Visualization in Medicine and Biology. Book Chapter in: Handbook of Medical Imaging: Processing and Analysis, ed. Isaac N. Bankman, Academic Press, San Diego, CA, Chapter 42, pp. 685-671 (2000).
Robinson, Advances in Multi-Modal Data Analysis: The ANA-LYZE Software Environment, httlp:/www.ii.metu.edu.tr/~med-ii/makaleler/analyze <http://www.ii.metu.edu.tr/~med-ii/makaleler/analyze>_sw_enve.pdf, 5 pages. Downloaded on Aug. 10, 2004.
Search Report for European Application No. 08783253.1 mailed Dec. 30, 2011 (7 pages).
Search Report for European Patent Application No. 06790638.8, mailed Apr. 23, 2010 (7 pages).
Simpson, R.G. et al. A 4-MV CT scanner for radiation therapy: The prototype system. Med. Phys. 9(4), Jul./Aug. 1982, pp. 574-579.
Soffen E.M. et al. Conformal static field radiation therapy treatment of early prostate cancer versus non-conformal techniques: A reduction in acute morbidity. Int J Radiat Oncol Biol Phys, 24: 485-488 (1992).
Supplementary European Search Report dated Oct. 25, 2010 (5 pages).
Supplementary European Search Report dated Oct. 30, 2008 for European Patent Application No. 05788508.9/PCT/CA2005001428.
Supplementary European Search Report for PCT/CA2005001106_RNM-003PC_dated Nov. 10, 2009, 6 pages.
Supplementary European Search Report, for PCT Application No. PCT/CA2005001135, dated Feb. 27, 2009 (12 pages).
Supplementary Partial European Search Report for EP Application No. 5763463 dated Nov. 30, 2009, 7 pages.
Swindell, W. et al. Computed tomography with a linear accelerator with radiotheraphy applications, Med. Phys. 10(4), Jul./Aug. 1983, pp. 416-420.
Thayananthan, A. et al., <http://mi.eng.cam.ac.uk/~bdrs2/papers/thayananthan> cvpr03.pdf, pp. 1-8. Downloaded from the Internet on Aug. 10, 2004.
Tome et al., Commissioning and Quality Assurance of an Optically Guided Three-dimensional Ultrasound Target Localization System for Radiotherapy, Med. Phys., 29(8):1781-1788 (2002).
Troccaz, J. et al. Conformal external radiotherapy of prostatic carcinoma: requirements and experimental results, Radiotherapy and Oncology 29 (1993) pp. 176-183.
Troccaz., J et al. Patient Setup Optimization for External Conformal Radiotherapy, Journal of Image Guided Surgery, 1, pp. 113-120 (1995).
Van de Geijn, J. et al. A Graticule for Evaluation of Megavolt X Ray Port Films, Radiation Oncology Biology Physics, Nov. 1982, vol. 8, No. 11 pp. 1999-2000.
Written Opinion of the International Search report for PCT/CA2005/001105 dated Oct. 27, 2005.
Written Opinion of the International Searching Authority for International Application No. PCT/CA2005/001106 dated Oct. 25, 2005.
Written Opinion of the International Searching Authority for PCT/CA2005/001428 dated Nov. 8, 2005 (6 pages).
Written Opinion of the International Searching Authority for PCT/CA2006/001289 dated Oct. 30, 2006 (6 pages).
Written Opinion of the International Searching Authority for PCT/CA2006/001461 dated Dec. 8, 2006 (5 pages).
Written Opinion of the International Searching Authority for PCT/CA2007/000898 dated Jul. 23, 2007 (6 pages).
Zhang, Iterative Point Matching for Registration of Free-Form Curves and Surfaces, International Journal of Computer Vision, 13(2):119-152 (1994).
Zitova, B. et al., Image Registration Methods: A survey, Image and Vision Computing, Elsevier, Guildford, GB, vol. 21, No. 11, Oct. 1, 2003 (24 pages).

* cited by examiner

INCORPORATING INTERNAL ANATOMY IN CLINICAL RADIOTHERAPY SETUPS

CROSS-REFERENCE TO RELATED APPLICATIONS

This application claims priority to and the benefit of, and incorporates herein by reference, in its entirety, provisional U.S. patent application Ser. No. 60/844,163, filed Sep. 13, 2006.

TECHNICAL FIELD

This invention relates to methods and systems for improving clinical setups in radiotherapy.

BACKGROUND INFORMATION

External beam radiotherapy for breast cancer is typically delivered by opposing tangential fields which provide a uniform dose to the entire affected breast. The treatment is given over a number of sessions, and is often followed by additional boost sessions. The boost sessions are typically delivered with an electron beam, which is designed to treat the primary lumpectomy site only.

Unlike photons, whose intensity decreases in an approximately exponential fashion within the patient, electrons deposit most of their dose within a fixed, finite range which depends on the energy of the beam. Thus, a single electron beam can be used to treat superficial lesions while sparing underlying healthy tissues. Electron treatments are delivered with electron cones of various sizes and shapes that are typically attached to the collimator of a linear accelerator, and which shape the electron beam very close to the patient surface. The shapes can be standard geometric shapes, such as circles or squares of various sizes, or an arbitrary shape can be custom-made for a given patient. In some instances, a lead sheet having an opening that defines the aperture of the beam is placed directly on the patient's skin.

Electron treatments are usually planned with a fixed source-to-skin distance (SSD). Breast boosts (a radiotherapy treatment in which a "boost" of 10-16 Gy of radiotherapy is given in addition to the normal radiotherapy treatment after surgery) typically use an SSD of 100 cm, as this is the same distance from the beam source to the isocenter of most linear accelerators ("linacs"). As a result, the linac isocenter, and hence the intersection of any wall lasers being used to align the patient with the linac, lies on the patient skin surface. This is in contrast to many photon treatments, which are planned such that the isocenter is near the center of the treatment volume.

For a breast boost, the electron field ideally should cover the tumor bed and the surgical path leading from the tumor bed to the surgical scar, plus a 1-2 cm margin. In addition, it is preferable to avoid the areola. Unfortunately, the location of the scar, which is used often as a proxy for the lumpectomy site to aim the electron beam, is often a poor indicator of the actual location of the underlying tumor bed. Ultrasound has been used for planning purposes to obtain the size and shape of the tumor bed, or seroma, which is the fluid-filled region of the lumpectomy site. Surgical clips, placed during surgery around the lumpectomy site, are radio-opaque and have also been used as a proxy for the lumpectomy site for planning purposes. What is needed, however, is a methodology to incorporate internal information, e.g., the position and extent of seroma as observed in ultrasound images, into the conventional clinical setups (simulation and/or treatment) for electron breast boost treatments.

SUMMARY OF THE INVENTION

The present invention facilitates the combination of images of internal anatomical information (such as seroma) obtained using ultrasound with visual external cues in order to achieve accurate patient setups for the delivery of radiotherapy treatments. The following embodiments are primarily described in relation to electron breast boosts augmented with 3D ultrasound images, but the methods and devices described herein may be applied to any radiation-therapy clinical setup procedure, such as many types of electron boost treatments, or any clinical setup using other photon or proton radiation beams, for example.

In one aspect, the invention provides a method for displaying images used during the administration of radiation treatment therapy in which an image of internal anatomical features (such as a lesion and/or an organ) of the patient is combined with representations of external features. Specifically, an image (such as a 3D ultrasound image) is acquired. The image may, for example, be acquired while the patient is in an initial setup position for delivery of the radiotherapy. Representations of external features (which may be anatomical and/or artificial) may also be acquired and added to the image, such that the operator can view both the internal and external features in one image. The annotated image may be displayed, for example, on a visual display located in the treatment room in close proximity to the patient such that the operator can view the display while manipulating the position of the patient. Adjustments to various treatment parameters relating to the administration of radiation therapy are provided, and the displayed image is automatically updated based on the adjustments.

In embodiments in which the image is a 3D ultrasound, the image may be segmented using manual and/or automated techniques. The treatment parameters may include the positioning of a patient on a supporting device, the placement of the supporting device itself, a beam angle, a beam shape and/or the placement of a radiation source relative to the patient.

In conjunction with the display of the image, the motion of the patient support device (e.g., a treatment couch), and the gantry and collimator angles of the linac, can be tracked automatically by a tracking system or, in some cases, can be entered directly via an input device (in some cases the display screen itself) by a technician. Features of the image can be manually or automatically contoured on the display while being presented to the technician from the point of view of the treatment beam ("beam's-eye view"). This image may be updated as the technician moves the gantry or the patient support. In this way, the technician can complete the clinical setup procedure using the visual cues of the patient/linac combination (e.g., a surgical scar, the areola, an en face beam, a fixed SSD) with the augmented information of the internal features of interest as seen on-screen (in real time or refreshed as needed).

Once the gantry and patient support device are correctly aligned to target the internal and external features, the invention facilitates the design of a treatment aperture, such as an electron cutout, to encompass both types of features. The technique can include drawing a desired treatment area or specific landmarks on the skin, drawing treatment areas or specific landmarks on the visual display, and/or transferring information between these two representations. In some embodiments, the transfer of features from skin to visual display is accomplished using a pointer tool tracked by an optical camera, or a camera system which directly images the drawn contours and transmits them to the visual display via a computer or network. In other embodiments, the transfer from visual display to skin is accomplished by printing information from the visual display to scale on a transparency, affixing the transparency to the electron cone, and tracing the cutout on the patient's skin. The resulting aperture can be built by, for example, creating cerrobend blocks for electron treatments.

In another aspect of the invention, a system for positioning a patient in preparation for the administration of radiation treatment therapy includes a register for receiving images of anatomical features of the patient and a processor for manipulating the images. The register receives both a diagnostic image (e.g., an ultrasound) of internal anatomical features of the patient as well as a representation of external features (either anatomical and/or artificial) of the patient. The processor annotates the diagnostic image with the representation of the external features and displays the resulting image to an operator. In response to instructions to adjust one or more treatment parameters relating to the administration of radiation treatment therapy, the processor updates the displayed image, thereby providing immediate and iterative feedback to the operator.

Another aspect of the invention provides a method for fabricating a radiation treatment aperture for a radiation treatment device. The method includes receiving an image of internal anatomical features of a radiotherapy patient during a treatment planning session, receiving a visual representation of external anatomical features of the patient, annotating the image with the visual representation and displaying the annotated image on a display in a manner such that the displayed image is presented as viewed by the radiation treatment device. A preferred profile for the radiation treatment aperture can then be traced on the display such that the preferred profile encompasses both the internal and external anatomical features, and the traced profile is then used as a template to fabricate the aperture.

In some embodiments, the patient may be placed on a treatment simulation device prior to obtaining the visual representation of the external anatomical features, and various treatment radiotherapy treatment parameters can then be adjusted, thereby aligning the visual representation of the external anatomical features with the diagnostic image. In certain implementations, the displayed image may be updated iteratively in response to the adjustments.

In yet another aspect, the invention provides a method for administering radiation treatment to a patient in which a diagnostic image of internal anatomical features and a representation of external features of the patient are received and the diagnostic image is annotated with the representation of the external features. The annotated image is presented on a display, and in response to the displayed annotated image, treatment parameters relating to the administration of radiation treatment to the patient are adjusted and the displayed annotated image is updated based on the parameter adjustments. The therapeutic radiation is then delivered to the patient in accordance with the displayed image.

BRIEF DESCRIPTION OF THE DRAWINGS

The foregoing and other objects, features, and advantages of the present invention, as well as the invention itself, will be more fully understood from the following description of various embodiments, when read together with the accompanying drawings, in which.

DETAILED DESCRIPTION

Figure 1:
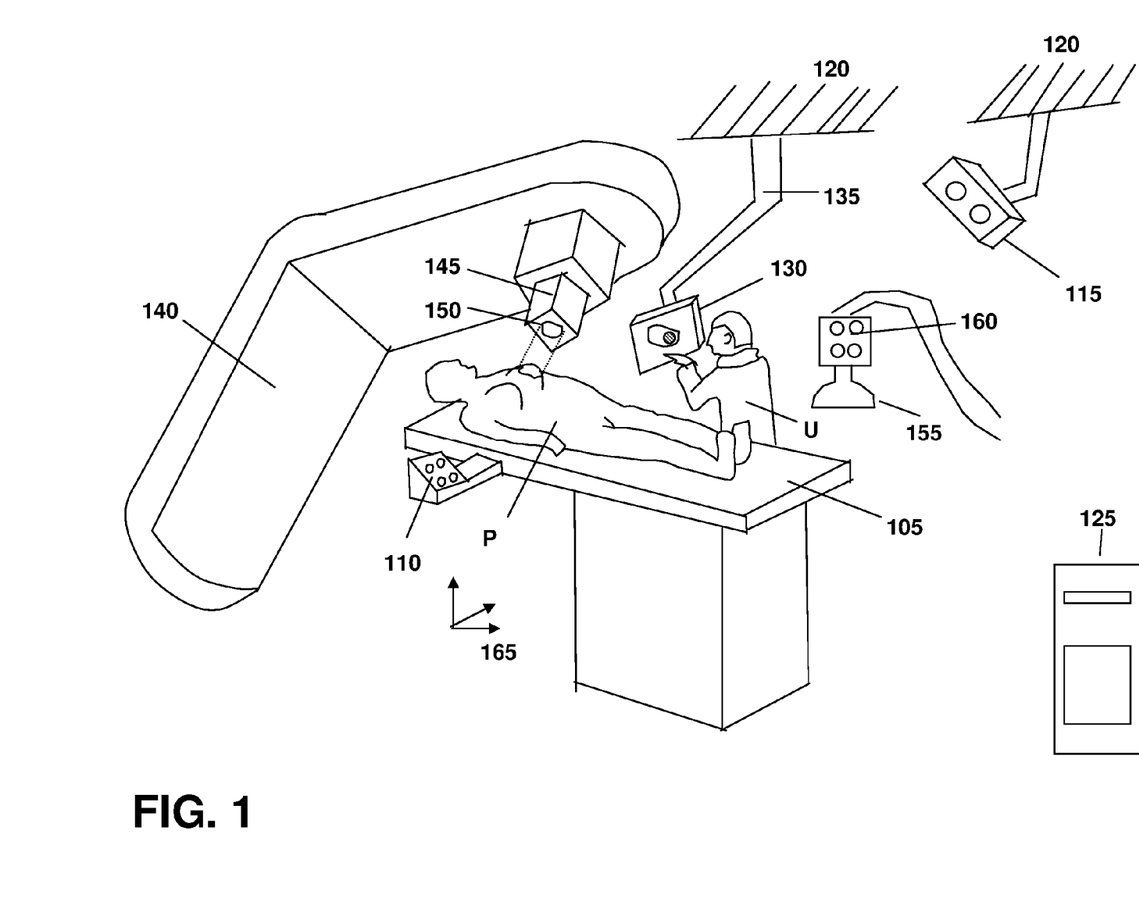
FIG. 1 depicts the delivery of radiotherapy to a patient in accordance with an embodiment of the invention.

FIG. 1 illustrates one embodiment of the invention in which a patient P is situated on a patient support device such as a treatment couch 105. The couch 105 is tracked using a set of reflecting or emitting markers 110, which are detected and monitored by an optical camera 115 attached to the ceiling 120 of the treatment room. Alternatively, the camera may be attached to other fixed and known positions in the room such as walls, beams and/or fixtures. The output of the camera 115 is transmitted (using wired or wireless channels) to a computer 125 having an associated visual display 130. In some instances, the computer 125 is located outside the treatment room to avoid radiation damage. The visual display 130 can be cart-based but is preferably mounted to a swing arm 135 attached to the ceiling 120, such that the user U (e.g., a radiation therapist, a dosimetrist, a medical physicist or a radiation oncologist) can move the visual display 130 to any convenient location. A linear accelerator 140 has affixed thereto an electron cone 145 that accepts an electron cut-out 150 to further collimate the electron beam. In some uses the linear accelerator 140 may be replaced by a conventional radiotherapy simulator or another treatment device. An ultrasound probe 155 with affixed emitting or reflecting markers 160 is also provided in the treatment room. The markers 160 are tracked by the optical camera 115, and thus a freehand sweeping motion of the probe over the underlying anatomy can acquire a series of 2D images, which with proper calibration can be reconstructed into a 3D image on the coordinate system 165 of the treatment room, which may be related to the isocenter of the linear accelerator 140.

Still referring to FIG. 1, during a pre-treatment simulation session the user obtains an ultrasound image of the patient's internal anatomy while the patient P is on a treatment couch 105 in a first position. For electron breast boosts, for example, the seroma or tumor bed is imaged. In some implementations a series of images may be combined to form a 3D ultrasound image. The 3D image (or slices thereof) obtained using the ultrasound device may then be displayed on the visual display 130. The user can define features of interest using various known segmentation algorithms (e.g., anatomical pattern recognition algorithms), if desired. For instance, the tumor bed can be contoured automatically. The user U can then change the treatment parameters by shifting and/or rotating the couch 105, and by rotating the linear accelerator gantry 140 and/or the collimator 150. These changes may then be transmitted to the computer 125 through either user input on the visual display 130, through direct connection with the control unit of the linear accelerator 140, or using a sensor to track objects attached to the couch 105 and/or linear accelerator 140. The computer 125 calculates the projection of the 3D image from the viewpoint of the treatment beam ("beam's-eye view"), and displays it on the visual display 130. The projected image can be updated each time the user changes the treatment angles or shifts the couch 105. In some cases contours, a lesion surface, and/or other landmarks may be shown in conjunction with the projected 3D image. The user places the patient on couch 105, and sets the desired gantry/collimator angles to encompass the features of interest in the 3D ultrasound image as well as the visual external features, such as surgical scars on the skin, and to avoid sensitive regions such as the areola. In the case of an electron boost, the user can also perform these tasks while ensuring that the beam is en face i.e., more or less perpendicular to the patient's skin, and at the prescribed SSD.

Electron breast boosts are often simulated directly on the linear accelerator, or a conventional simulator, rather than on a CT scanner. The physician uses the lumpectomy scar and palpation to determine the location of the lumpectomy site relative to the patient's skin. A cutout, usually made of cerrobend, is designed to cover the region of interest on the patient's skin. The gantry and couch angles are adjusted such that the beam is en face. The appropriate electron energy is then chosen such that the beam covers the depth of the tumor bed, which may be found from post-surgery ultrasound scans, for example. Using conventional techniques, the correct number of "Monitor Units" required to deliver a percentage of the prescribed dose at a given depth is calculated from tabulated beam data.

The first radiation session, or fraction thereof, may be delivered immediately following the initial simulation, or on a subsequent day. For each fraction, the setup may be adjusted so that the field covers the same skin surface area as planned, and to ensure that the beam is en face. These adjustments are often necessary because it is difficult to reposition the breast in exactly the same way from day to day, and are typically accomplished by changing the gantry angle and/or couch position. This patient setup is often referred to as a "clinical setup" since it is adjusted based on external and/or palpable features of the patient and additional clinical knowledge of disease.

In some institutions the simulation is performed using computed tomography simulation (CT-Sim) rather than a clinical setup. One method is to place radio-opaque wire around the surgical scar, and sometimes the areola, prior to the acquisition of a CT scan. Thus the scar and the lumpectomy site, as seen on the CT scan, can be used to design the electron field. The daily patient setup is still typically done clinically, i.e. the gantry/couch angles are not necessarily taken as calculated from the treatment plan but instead are adjusted for the patient immediately prior to treatment.

Figure 2:
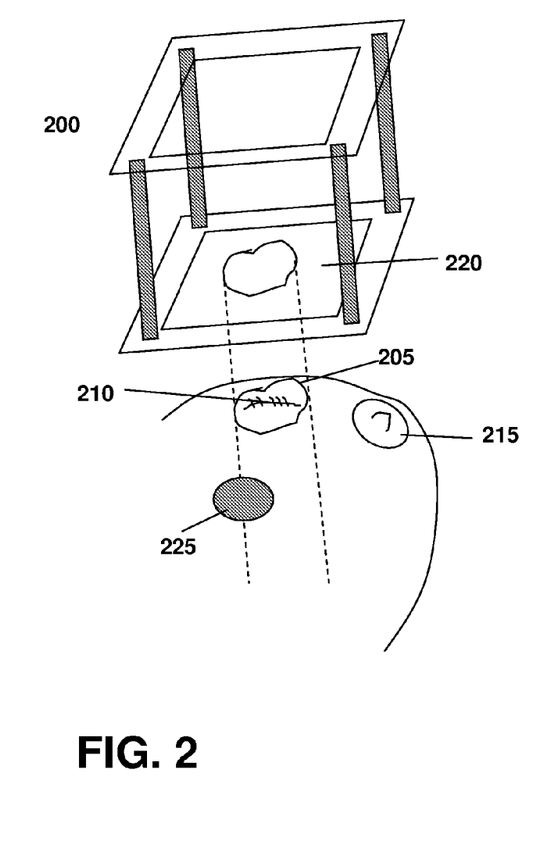
FIG. 2 depicts the use of a profile aperture as applied to a diagnostic or treatment delivery device in accordance with an embodiment of the invention.

In some embodiments, the invention can be used to generate field apertures, such as design electron cutouts, which incorporate both internal anatomy as acquired by the image, and visual features on the skin. Referring to FIG. 2, an electron cone 200 is set at the position as described above. Conventionally, the physician would draw a contour 205 of the treatment region directly on the patient's skin to encompass visible features such as a surgical scar 210. In drawing this contour 205, the physician may also incorporate other knowledge from diagnostic scans acquired at earlier times or surgical reports, and avoid sensitive areas such as the areola 215. An electron cut-out 220 (also referred to as an aperture or profile) may then be designed such that it corresponds to the drawn contour by, for example, placing a transparent fiberglass plate in the cutout tray and drawing on the plate such that the shadow reproduces the line drawn on the patient's skin. The fiberglass plate may then be used to fabricate a cerrobend cutout to be used during the treatment procedure. Using this approach, however, the cutout may miss all or part of the lumpectomy site 225 and thereby reduce the effectiveness of the treatment.

To address this and other shortcomings of the conventional methods, the present invention facilitates preparation of an improved cutout having a preferred profile incorporating both the visual cues and observations of the patient's internal anatomy. In particular, the invention facilitates transmitting information between the screen and the patient's skin, and vice-versa, in order to combine data from the two sources. As a result, the user can not only create a more accurate cutout, but also iteratively adjust multiple treatment and positioning parameters in parallel and see the results of these changes in real time. By contrast, if the cutout were merely drawn on the screen to encompass the lumpectomy site, it might not cover the skin landmarks appropriately.

With renewed reference to FIG. 1, the visual screen 130 displays a projection of the internal anatomy from the perspective of the electron cone attached to the linac beam. To transmit information on the skin to the screen, a tracked pointer tool may be used to digitize points on the skin surface. The pointer can, for example, have markers affixed thereto which can be tracked with the optical camera 115. The device may be calibrated using known calibration techniques such that the position of the tip in a known coordinate system is transmitted to the computer 125 for reference. Thus, features on the skin surface, such as the physician-drawn contour 205, the scar 210 and/or the areola 215 of FIG. 2 can be transmitted to the computer 125 and displayed along with the 3D ultrasound on the visual display 130 relative to the lumpectomy site. The cutout can thus be designed on the screen, incorporating information obtained from an image of the patient's internal anatomy and external features. Alternatively, the transfer of information from skin to screen can be performed with a camera system by extracting a snapshot of the features, digitizing the images, and converting pixels in the image to 3D points in the reference coordinate system.

To transmit information from the screen to the patient's skin, a number of techniques can be used. One approach, for example, is to print a scaled version of the beam's-eye-view projection shown on the visual display 130 onto a transparency using a printing device. The transparency may then be mounted on the cutout holder of the linac 140, thus producing a shadow on the patient's skin which may then be traced with a marker. Another approach employs a calibrated laser scanner mounted in the treatment room or directly on the electron cone. The scanner continuously directs the laser beam along the screen contour's shape fast enough so that it appears as a continuous outline on the patient's skin, which again may be traced with a marking implement. Still another approach uses radio-opaque leaves that are placed in the electron cone 145 and mechanically driven by servo motors to form the correct shape on the patient's skin using the light field from the linear accelerator head. The outline of the light field is traced onto the patient's skin. Finally, as described in U.S. Pat. No. 6,317,616, it is possible to use an LCD screen in the path of the light emitted from the head of the linear accelerator 145.

In many cases, simple shapes such as circles and squares are used for electron cut-outs. Such shapes of predetermined size can be selected on the visual display to encompass the lumpectomy site. A corresponding pre-made cutout can then be placed in the electron cone, to see if it also covers the correct region on the skin. This process can be repeated iteratively until an adequately sized cutout is obtained to cover both skin and internal information. The cutout information can be viewed on the skin during the simulation process, or it can be viewed the next day after the actual cut-out has been manufactured or at the first treatment fraction.

Thus, a representation of the visual-surface cues such as the scar and/or the areola may be digitized and used to design a cut-out using a pointer tool as describe above. Both a representation of the internal lumpectomy site as extracted from the ultrasound data and the visual cues may be displayed together, preferably in a projection that mirrors the beam's-eye view of the linac. A model of the cut-out can be designed directly on the visual display or at another computer workstation and used, either as a manual template or to guide an automated cutting device in order to physically fabricate the cut-out.

Figure 3:
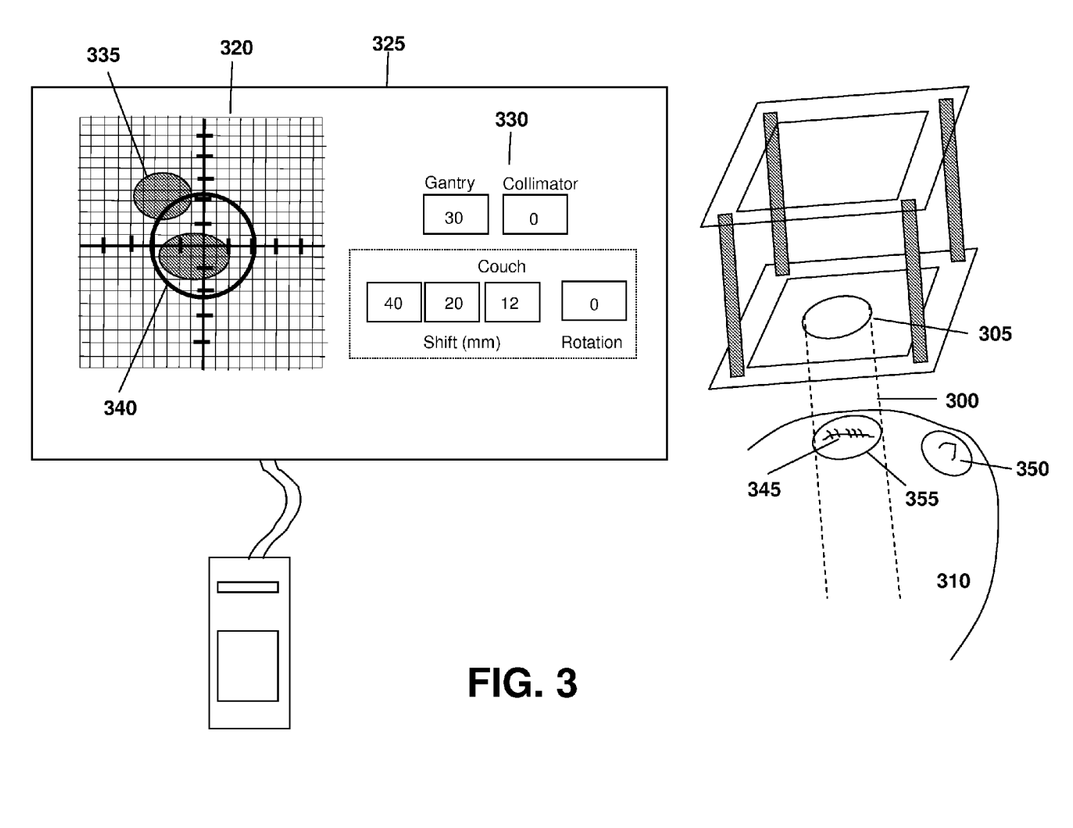
FIG. 3 depicts various treatment parameters and images obtained using the profile aperture of FIG. 2 in accordance with an embodiment of the invention.

The above-described embodiments involving the determination of treatment angles and patient positioning are useful in clinical setups for both simulations and treatment sessions, whereas the design of cut-outs is primarily useful in the simulation session. In some embodiments, however, the cut-out, once designed, may be superimposed on the beam's-eye view shown on the visual display during patient setup. Referring to FIG. 3, an electron beam 300 of a certain angle, with cut-out 305, is projected onto the breast 310 of a patient at a given couch position. During a previous planning stage, simulation stage, or some other previous time, an ultrasound of the lumpectomy site was acquired and contoured using manual or automated techniques. That previously acquired ultrasound image is displayed along with the beam's-eye view projection 320 on the display 325. The gantry, collimator and couch angles of the physical setup 330 (indications of which may also be indicated on the display screen), and the contoured tumor bed 335 are considered when displaying the ultrasound image. The cut-out 305 is represented on the beam's-eye view projection image 320 as indicated at 340. Initially, it is likely that the tumor bed 335 will not be encompassed within the projection of the cut-out 340. To compensate, the user adjusts the couch, beam angle, or other positioning and/or treatment parameters, and can obtain immediate visual feedback of the adjustments on the display screen. Because visual cues such as the scar 345, areola 350, skin marking 355 and skin surface, as well as the internal information as captured by the ultrasound can be seen in real-time on the display, the user can consider all of these factors in parallel while also ensuring that the SSD is correct and that the beam is en face. While these adjustments are made, the projection angle of the beam's-eye view may also be adjusted to account for the current physical orientation of the gantry and collimators. As a result, the user can immediately see how the various adjustments affect the delivery of the beam as it relates to both external and internal markings and/or anatomical structures—e.g., how well the cutout 340 aligns with the tumor bed 335. The process can continue repeatedly until the physician is satisfied that the treatment parameters are appropriate or until some predefined treatment goal (e.g., some percentage coverage of a lesion and associated scar tissue) has been reached.

In some embodiments, a portion of the structure supporting the linac in the direction parallel to the beam is shown so that the user can calculate the depth of the lumpectomy and the electron energy required to treat it. A computer may calculate the energy from the depth directly using, for example, data tables or modeling equations. During a treatment session, the depth of the site is typically primarily be used as a verification that the site is covered rather than for the selection of a new energy.

Although embodiments of the invention are described above primarily with reference to three-dimensional images, medical applications often require the segmentation of images obtained using other modalities such as CT, MRI, PET, SPECT or two-dimensional ultrasound. In cases in which the image is a three-dimensional image, the image can be separated into one or more sets of two-dimensional images such as parallel slices or rotational slices about an axis of rotation.

Figure 4:
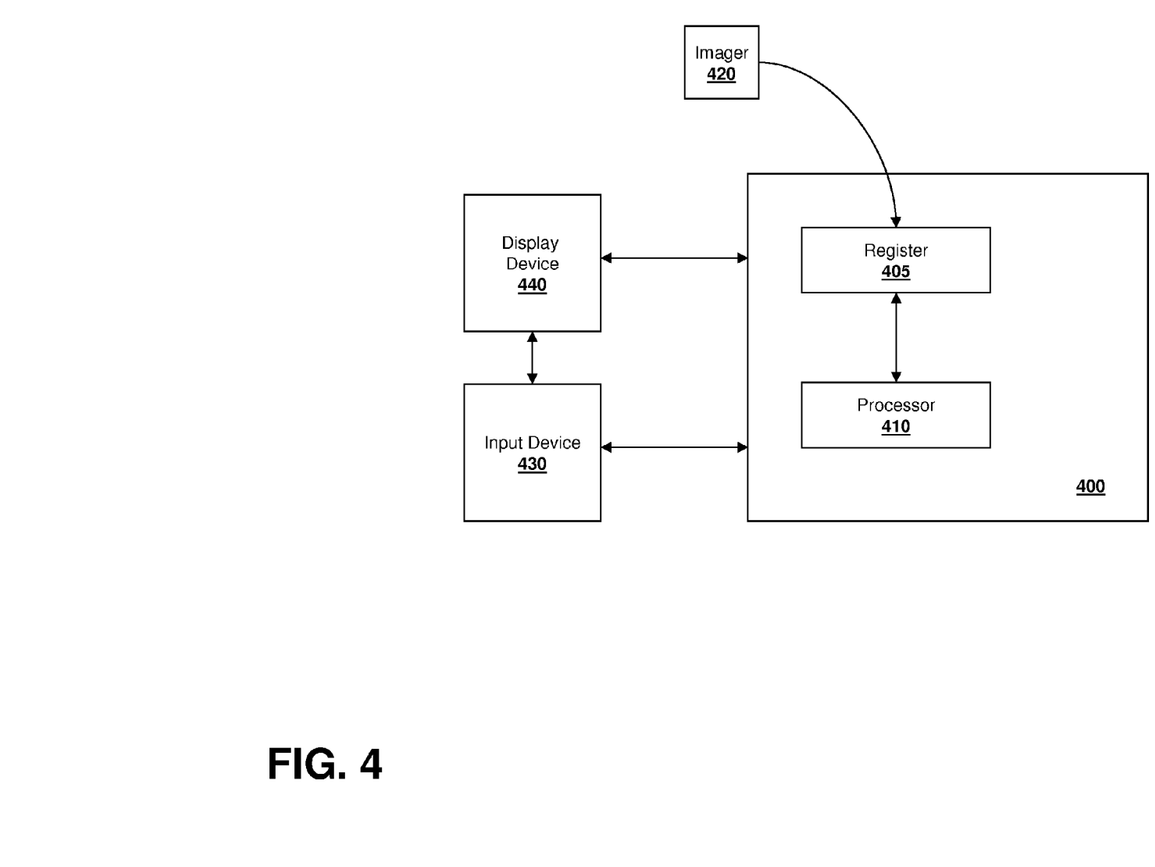
FIG. 4 schematically depicts a system for presenting images used in the delivery of radiotherapy in accordance with an embodiment of the invention.

FIG. 4 schematically depicts a hardware embodiment of the invention realized as a system 400 for combining diagnostic images of internal anatomical features of a patient with representations of external features to facilitate patient positioning. The system 400 comprises a register 405 and a processor 410.

The register 405, which may be any suitably organized data storage facility (e.g., partitions in RAM, etc.), receives images from an imager 420 such as an MRI, CT/PET scanner, ultrasound device, or x-ray device. In some embodiments, the images are stored on a data-storage device separate from the imager (e.g., a database, microfiche, etc.) and sent to the system 400. The register 405 may receive the images through conventional data ports and may also include circuitry for receiving analog image data and analog-to-digital conversion circuitry for digitizing the image data.

The register 405 provides the image to processor 410, which implements the functionality of the present invention in hardware or software, or a combination of both on a general-purpose computer. Where manual input and manipulation is used, the system 400 receives instructions from a user via an input device 430 such as a mouse or other pointing device. The images can be viewed using a display device 440 such as a computer display screen or hand-held device.

In addition, such a program may set aside portions of a computer's random access memory to provide control logic that affects one or more of the image acquisition, manipulation, annotation, and display. In such an embodiment, the program may be written in any one of a number of high-level languages, such as FORTRAN, PASCAL, C, C++, C#, Java, Tcl, or BASIC. Further, the program can be written in a script, macro, or functionality embedded in commercially available software, such as EXCEL or VISUAL BASIC. Additionally, the software can be implemented in an assembly language directed to a microprocessor resident on a computer. For example, the software can be implemented in Intel 80x86 assembly language if it is configured to run on an IBM PC or PC clone. The software may be embedded on an article of manufacture including, but not limited to, "computer-readable program means" such as a floppy disk, a hard disk, an optical disk, a magnetic tape, a PROM, an EPROM, or CD-ROM.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A method for positioning a patient prior to administration of an electron treatment using a linear accelerator, the method comprising:
    obtaining a three-dimensional (3D) diagnostic image of a patient situated on a patient support device prior to the electron treatment;
    segmenting the 3D diagnostic image to define an internal anatomical feature within a patient's breast;
    annotating the segmented image to identify an external feature on a surface of the patient's skin;
    displaying the annotated image from a beam's-eye vie of the linear accelerator;
    iteratively modifying the physical setup of the patient by at least one of rotating a gantry of the linear accelerator and adjusting the patient support device until the internal and external features are aligned;
    updating the display to show a perspective of the beam's-eye view in response to the modification of the treatment parameter until a direction of an electron beam of the linear accelerator is aligned along the beam's-eye view to the internal feature; and
    directing a single electron beam of the linear accelerator along the beam's-eye view toward the internal feature.

2. The method of claim 1, wherein the internal anatomical feature comprises at least one of a lesion, a seroma, a tumor, a fibrosis, and a tumor bed.

3. The method of claim 1, wherein the external anatomical feature comprises at least one of a surface landmark, an areola, a lumpectomy location, a surgical scar, a fiducial marking, and a skin marking.

4. The method of claim 1, wherein the physical setup of the patient comprises at least one of a position of the patient on the patient support device, a placement of the patient support device, a beam angle, a beam shape, a shift in the patient support device, a rotation of the patient support device, a gantry rotation, a collimator rotation, a change in a collimator angle, a change in a treatment angle, a change in the beam's-eye view, and a placement of a radiation source relative to the patient.

5. The method of claim 1, further comprising modifying the physical setup of the patient to align the internal feature with the beam's-eye view while determining when a predetermined percentage coverage of a lesion is achieved as shown in the display.

6. The method of claim 1, wherein obtaining further comprises obtaining a two-dimensional (2D) image, wherein the 2D image comprises a 2D rotational slice about an axis of rotation.

7. The method of claim 1, wherein the radiation treatment comprises an electron boost treatment for the breast of the patient.

8. The method of claim 1, wherein a treatment beam is approximately perpendicular to the patient's skin.

9. The method of claim 1, further comprising
    fabricating a treatment aperture based on the internal and external features, wherein the treatment aperture has a customized shape.

10. The method of claim 1, wherein the diagnostic image comprises at least one of an ultrasound image, a computed tomography image, and a magnetic resonance image.

11. The method of claim 1, wherein the physical setup of the patient comprises a distance from the linear accelerator to a skin surface.

12. The method of claim 1, wherein adjusting the patient support device comprises shifting or rotating the patient support device.

13. The method of claim 1, wherein iteratively modifying comprises rotating a collimator of the linear accelerator.

14. The method of claim 1, wherein the beam's-eye view is adjusted to compensate for a physical position of the gantry.

15. The method of claim 1, wherein the beam's-eye view is adjusted to compensate for a physical position of a collimator.

16. The method of claim 1, wherein updating the display to show the perspective of the beam's-eye view comprises displaying the perspective on the display, and wherein the displayed perspective is based on a gantry angle, a patient support device position, and a patient support device angle.

17. The method of claim 1, wherein an angle of the gantry and an angle of the patient support device are adjusted prior to treating the patient with the single electron beam.

18. The method of claim 1, wherein the patient's physical setup comprises a predetermined distance from a linear accelerator source to a skin surface distance.

19. The method of claim 1, wherein the physical setup of the patient further comprises at least one of a collimator angle, a gantry angle, a patient support device angle, and a patient support device position.

20. The method of claim 1, wherein the external feature is a digitized surface landmark.

21. The method of claim 1, wherein the treatment beam is approximately en face.

* * * * *

UNITED STATES PATENT AND TRADEMARK OFFICE
CERTIFICATE OF CORRECTION

PATENT NO. : 9,451,928 B2
APPLICATION NO. : 11/852492
DATED : September 27, 2016
INVENTOR(S) : Tony Falco et al.

Page 1 of 1

It is certified that error appears in the above-identified patent and that said Letters Patent is hereby corrected as shown below:

Claim 1, Column 9, Line 11, "beam's-eye vie" should read --beam's-eye view--.

Signed and Sealed this
Seventeenth Day of January, 2017

Michelle K. Lee
*Director of the United States Patent and Trademark Office*